United States Patent
Chang et al.

(10) Patent No.: US 8,109,959 B2
(45) Date of Patent: Feb. 7, 2012

(54) BLOOD SAMPLING NEEDLE

(75) Inventors: Fu-Nan Chang, Taoyuan (TW); Yen-Hung Liu, Taoyuan (TW)

(73) Assignee: Profession Enterprises, Co., Taoyuan, Taoyuan County (TW)

( * ) Notice: Subject to any disclaimer, the term of this patent is extended or adjusted under 35 U.S.C. 154(b) by 165 days.

(21) Appl. No.: 12/699,212

(22) Filed: Feb. 3, 2010

(65) Prior Publication Data
US 2011/0066077 A1    Mar. 17, 2011

(30) Foreign Application Priority Data
Sep. 16, 2009    (TW) .............................. 98217044 U

(51) Int. Cl.
*A61B 17/14* (2006.01)
(52) U.S. Cl. ........................................ 606/181; 600/573
(58) Field of Classification Search .................. 606/181, 606/182; 600/573, 576, 583
See application file for complete search history.

(56) References Cited

U.S. PATENT DOCUMENTS

| | | | | |
|---|---|---|---|---|
| 5,643,222 A | * | 7/1997 | Mahurkar | 604/195 |
| 7,470,238 B2 | * | 12/2008 | Sakata et al. | 600/583 |
| 2009/0043324 A1 | * | 2/2009 | Paschal | 606/181 |

* cited by examiner

*Primary Examiner* — Victor Nguyen
(74) *Attorney, Agent, or Firm* — Egbert Law Offices PLLC

(57) ABSTRACT

A blood sampling needle has a shell, a trigger seat, a needle stand, an elastic resetter and a safety switching member. The shell is provided with inner wall, retaining space, needle outlet and insertion end. A through-flange is formed into the shell. The through-flange and inner wall form a release groove with a tapered end-face. The trigger seat is mounted into the retaining space in a moveable state. The trigger seat has a control end and a rod. An axial chamber is opened on the rod so that two elastic release blades are formed on the rod, and also accommodated correspondingly into the release groove. An abutting bevel edge is formed at the bottom of the elastic release blade, and mated with the tapered end-face of the release groove in an oblique surface. The present invention saves structural members, reduces fabrication cost with better safety and applicability.

6 Claims, 6 Drawing Sheets

BLOOD SAMPLING NEEDLE

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates generally to a blood sampling needle, and more particularly to an innovative one which enables users to simplify the structural members, save the fabrication cost and improve the operational safety.

2. Description of Related Art Including Information Disclosed Under 37 CFR 1.97 and 37 CFR 1.98.

Generally, a blood sampling needle comprises a shell, a spring, a pricker and a push rod. In order to increase the restoring force of the pricker, two elastic strips are arranged between the push rod and the shell, so that the pricker can be put back into the shell once completion of blood sample collection by the blood sampling needle. However, there still exist some shortcomings against the conventional blood sampling needle, such as complicated structure and high cost.

Furthermore, when the conventional blood sampling needle is used for blood collection, pulling out the needle should be firstly conducted, namely, users may push a push rod to a triggering position, and then press the trigger button for pricking and blood collection. But the push rod may be pushed unintentionally or by others to the trigger position, leading to unexpected pricking accidents and other hazards.

Thus, to overcome the aforementioned problems of the prior art, it would be an advancement if the art to provide an improved structure that can significantly improve the efficacy.

Therefore, the inventor has provided the present invention of practicability after deliberate experimentation and evaluation based on years of experience in the production and development of related products.

BRIEF SUMMARY OF THE INVENTION

The enhanced efficacy of the present invention is as follows:

Based on the unique configuration of the "blood sampling needle" of the present invention wherein a release groove with tapered end-face is arranged into the retaining space of the shell, the abutting bevel edge set for the elastic release blade of the trigger seat is mated with the tapered end-face of the release groove in an oblique surface. Thus, the trigger seat is mated with the oblique surface to support the elastic release blade for triggering the needle stand, helping to save the structural members and reduce the fabrication cost with better industrial benefits.

Moreover, based on the structure of the present invention wherein the locking bulge of the safety switching member is aligned with the limiting slot, the trigger seat of the blood sampling needle is under a moveable state, so the pricker can protrude out of the needle outlet of the shell for blood collection. Alternatively, the trigger seat can be also under a limiting state, so the blood sampling needle cannot be easily triggered, thus ensuring a higher degree of safety.

Based on the structure wherein the exterior of the insertion end of the shell and the control end of the trigger seat are of a multi-angular cross section, the exterior of the insertion end and the control end of the trigger seat can be mated, and the needle stand is under a triggering or limiting state, enabling the user to judge visually and identify easily the state of the blood sampling needle A.

Although the invention has been explained in relation to its preferred embodiment, it is to be understood that many other possible modifications and variations can be made without departing from the spirit and scope of the invention as hereinafter claimed.

DETAILED DESCRIPTION OF THE INVENTION

Figure 1:
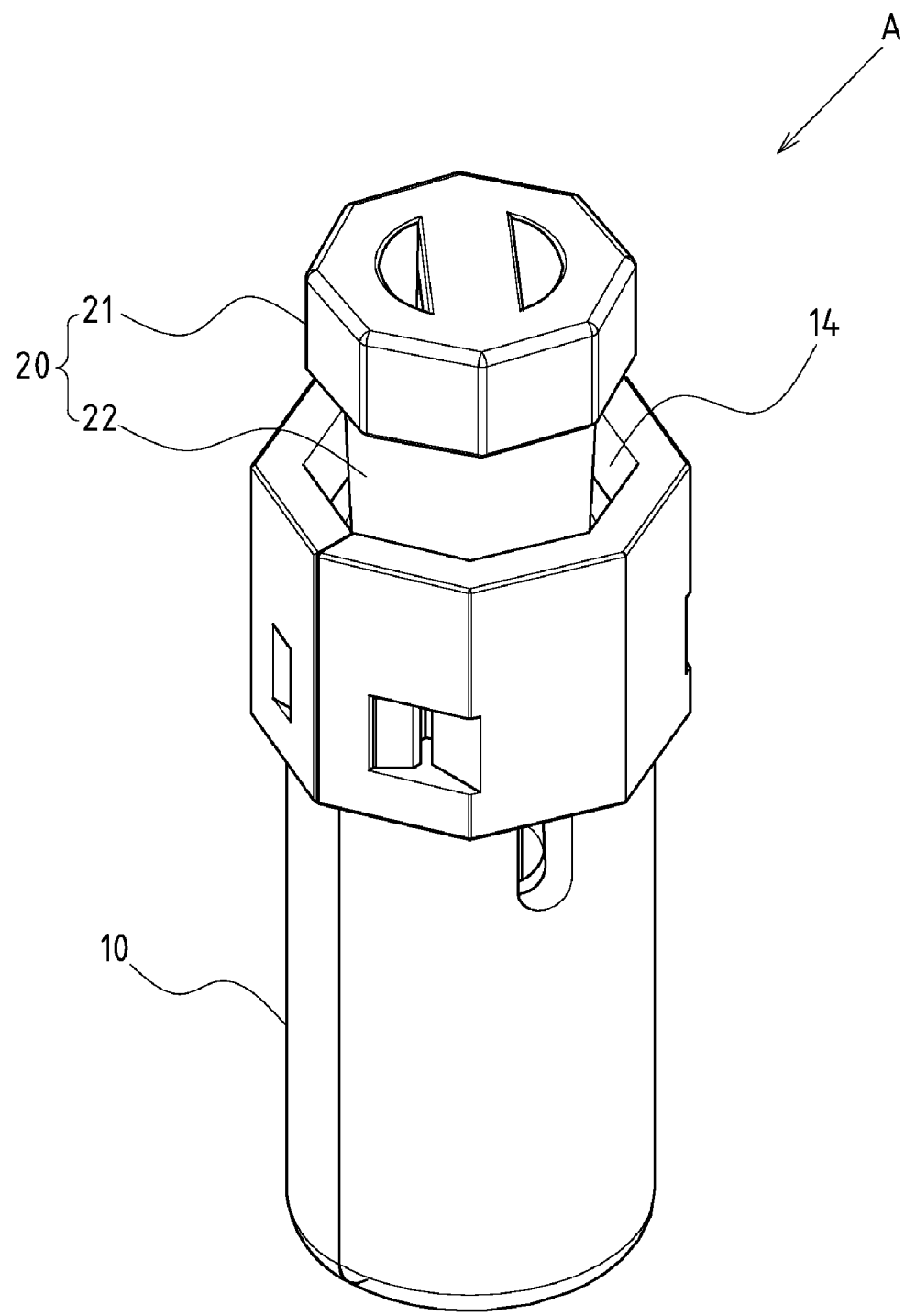
FIG. 1 shows a perspective view of the assembled preferred embodiment of the present invention.
Figure 2:
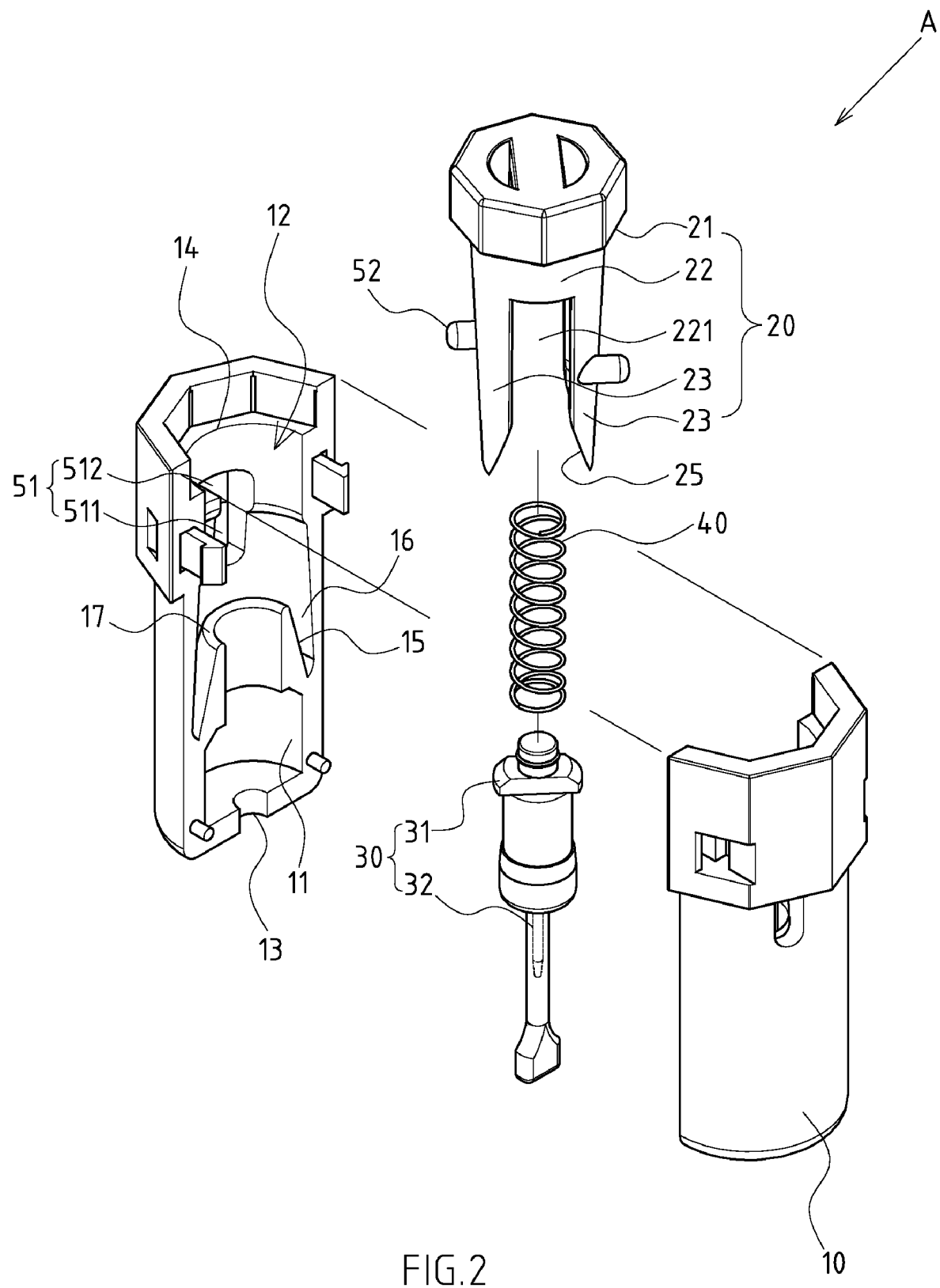
FIG. 2 shows an exploded perspective view of the preferred embodiment of the present invention.

FIGS. 1-4 depict preferred embodiments of a blood sampling needle of the present invention, which are provided for only explanatory objective for patent claims. Said blood sampling needle A includes a shell 10, comprising an inner wall 11 and a retaining space 12. A needle outlet 13 and an insertion end 14 are defined at both ends of the retaining space 12.

A release groove 16 has a tapered end-face 15. A through-flange 17 is protruded inwards from the inner wall 11 of the shell 10, and a tapered end-face 15 is formed on the through-flange 17 nearby the inner wall 11 of the shell 10, so that the tapered end-face 15 and inner wall 11 of the shell 10 form a release groove 16.

A trigger seat 20 is mounted into the retaining space 12 of the shell 10 in a moveable state. The trigger seat 20 comprises a control end 21 and a rod 22. An axial chamber 221 is opened on the rod 22 so that two elastic release blades 23 are formed on the rod 22. These two elastic release blades 23 can be accommodated correspondingly into the release groove 16.

An abutting bevel edge 25 is arranged at the bottom of the elastic release blade 23. Said abutting bevel edge 25 is mated with the tapered end-face 15 of the release groove 16 in an oblique surface, so that two elastic release blades 23 can be supported outwards and the needle stand 30 is released. Thus, the pricker 32 can rapidly puncture downwards until reaching outside the needle outlet 13 of the shell 10, then the skin of the testee can be punctured easily to facilitate the blood collection by the nursing staff.

A needle stand 30 has a coupling end 31 and a pricker 32, of which said coupling end 31 is assembled in the axial chamber 221 of the trigger seat 20.

An elastic resetter 40 is assembled between the axial chamber 221 of the trigger seat 20 and the needle stand 30. One end of the elastic resetter 40 is clamped by a snapping end 33 on the needle stand 30. Said elastic resetter 40 is normally under a state of accumulating preset elastic force, so that the needle stand 30 is driven to reset inwards after the elastic force of the elastic resetter 40 is released. Hence, the triggered pricker 32 will be automatically retracted into the axial chamber 221 of the trigger seat 20.

Figure 5:
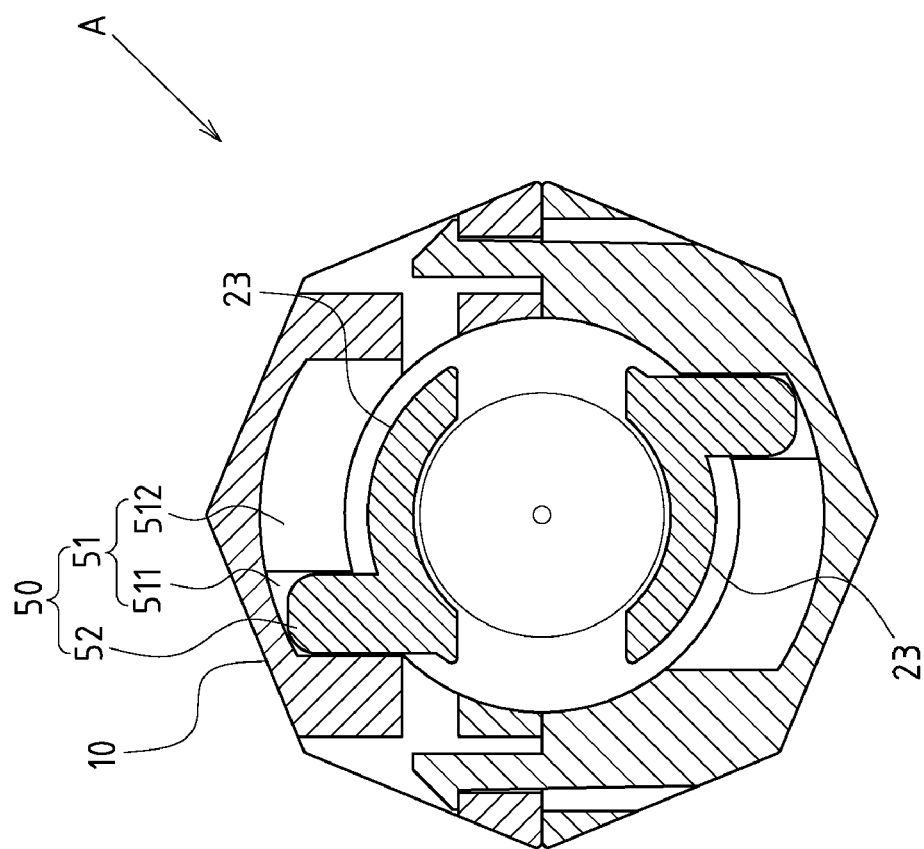
FIG. 5 shows a cross-sectional view of the present invention wherein the trigger seat is under a triggering state.

A safety switching member 50 enables the displacement of the trigger seat 20, and also allows the pricker 32 to protrude outside the needle outlet 13 of the shell 10 for puncturing the skin of testee, or limiting the movement of the trigger seat 20 so as to prevent the triggering of the blood sampling needle A (marked in FIG. 5).

Figure 9:
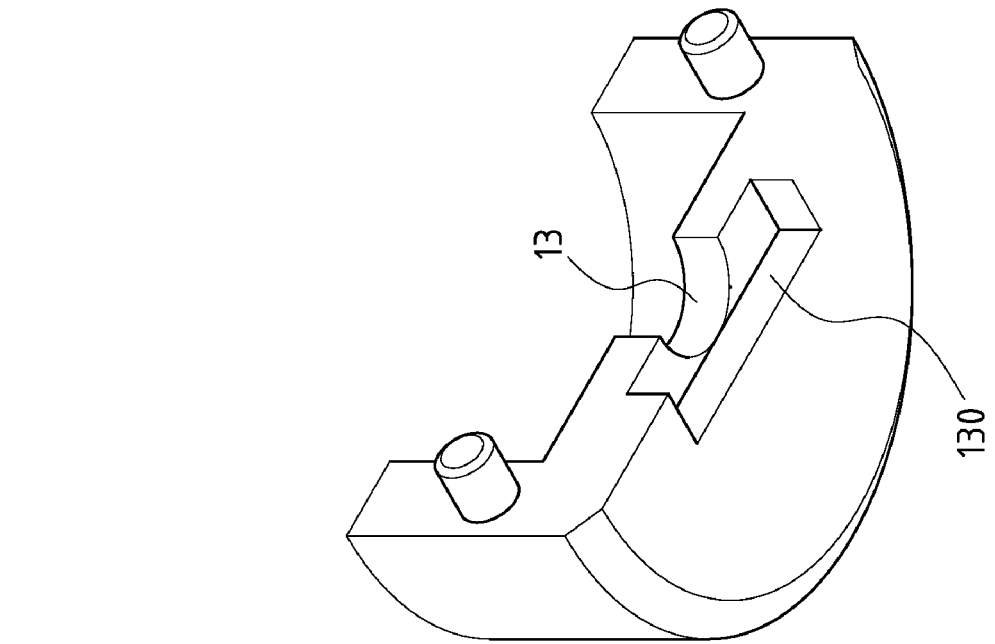
FIG. 9 shows a 3D schematic view of the present invention wherein the needle outlet is provided with a limiting slot.
Figure 8:
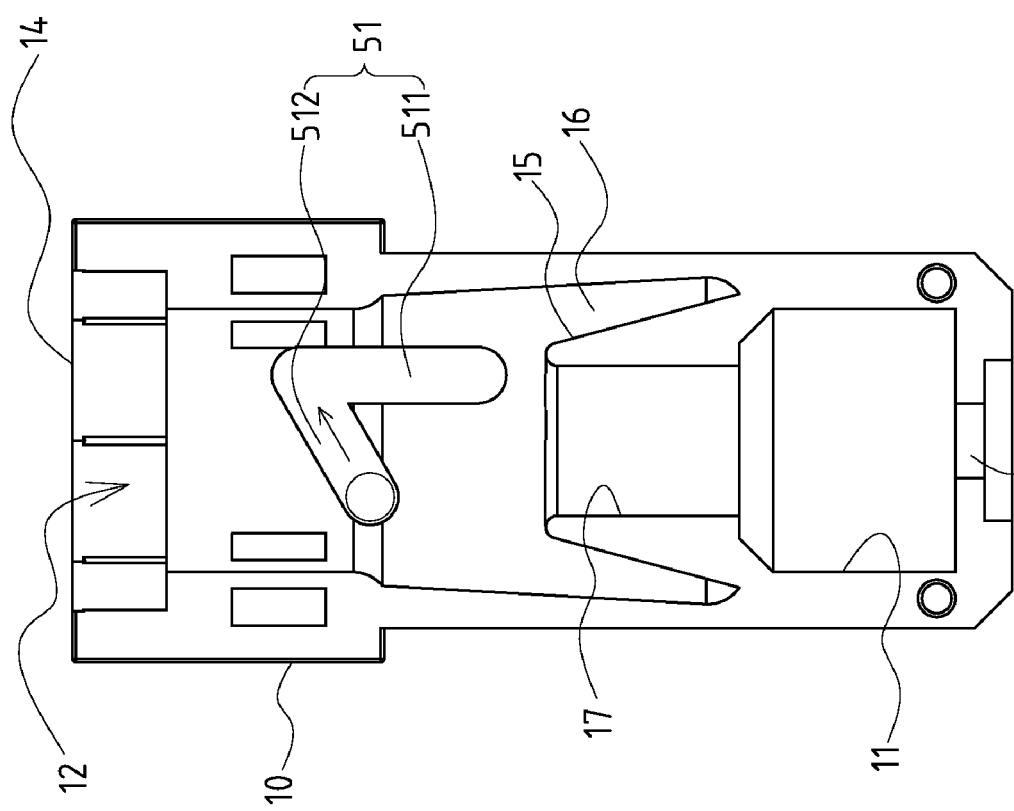
FIG. 8 shows a schematic view of the present invention wherein the annular dent is arranged transversely.

Referring to FIG. 5, the safety switching member 50 comprises a limiting slot 51 and two locking bulges 52. Said limiting slot 51 is formed on the inner wall 11 of the shell 10, and said locking bulges 52 are arranged onto the wall of the rod 22 of the trigger seat 20 correspondingly to the axial chamber 221. The L-shaped limiting slot 51 is defined to form an axial dent 511 and an annular dent 512. The annular dent 512 of the limiting slot 51 is arranged transversely (shown in FIG. 8). In this preferred embodiment, the bottom of the pricker set 34 is of an expanded rectangular body, which can be snapped into the limiting slot 130 of the needle outlet 13 (shown in FIG. 9). When the locking bulges 52 shift transversely along the path of the annular dent 512, the needle stand 30 is driven upwards to be disengaged from the pricker set 34, thus enabling users to remove easily the pricker set 34.

Of which, both ends of the elastic resetter 40 are separately connected with the snapping end 33 of the needle stand 30 and a boss 222 set on the axial chamber 221 of the control end 21 of the trigger seat 20.

A shoulder 223 is formed on the axial chamber 221 of the trigger seat 20, so as to support the coupling end 31 of the needle stand 30.

The exterior of the insertion end 14 of the shell 10 and the control end 21 of the trigger seat 20 are of a multi-angular cross section (shown in FIG. 1), so that the exterior of the insertion end 14 is mated with the control end 21 of the trigger seat 20, and the needle stand 30 is under a triggering or limiting state, enabling the user to judge visually the state of the blood sampling needle A.

Figure 7:
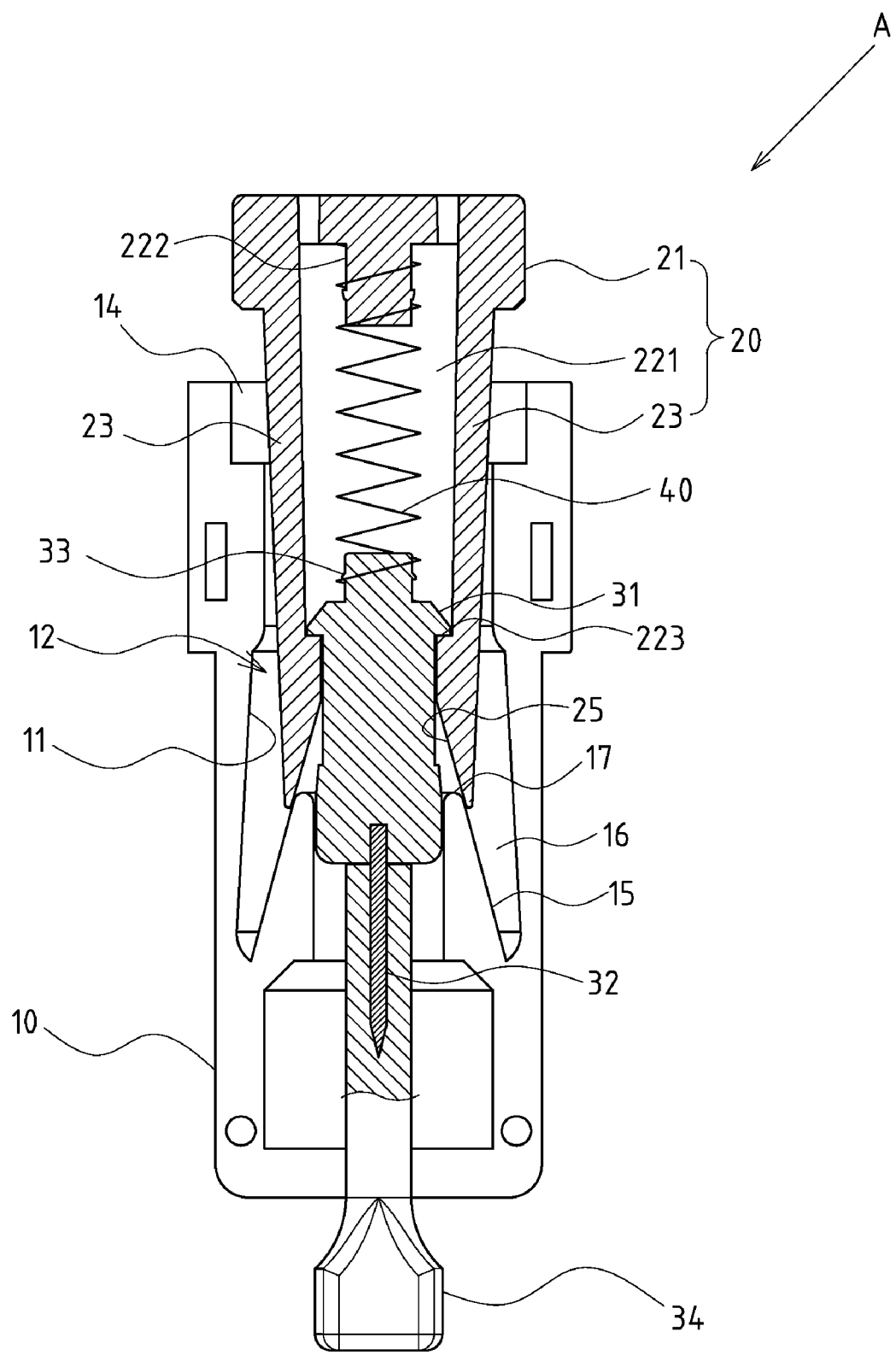
FIG. 7 shows a schematic view of the present invention wherein a pricker set is fitted additionally.

Referring to FIG. 7, the pricker set 34 is sleeved externally onto the pricker 32 of the needle stand 30 in such a way that the pricker set 34 is inserted towards the retaining space 12 from the needle outlet 13 of the shell 10, and then protruded out of the needle outlet 13 for protection.

Figure 3:
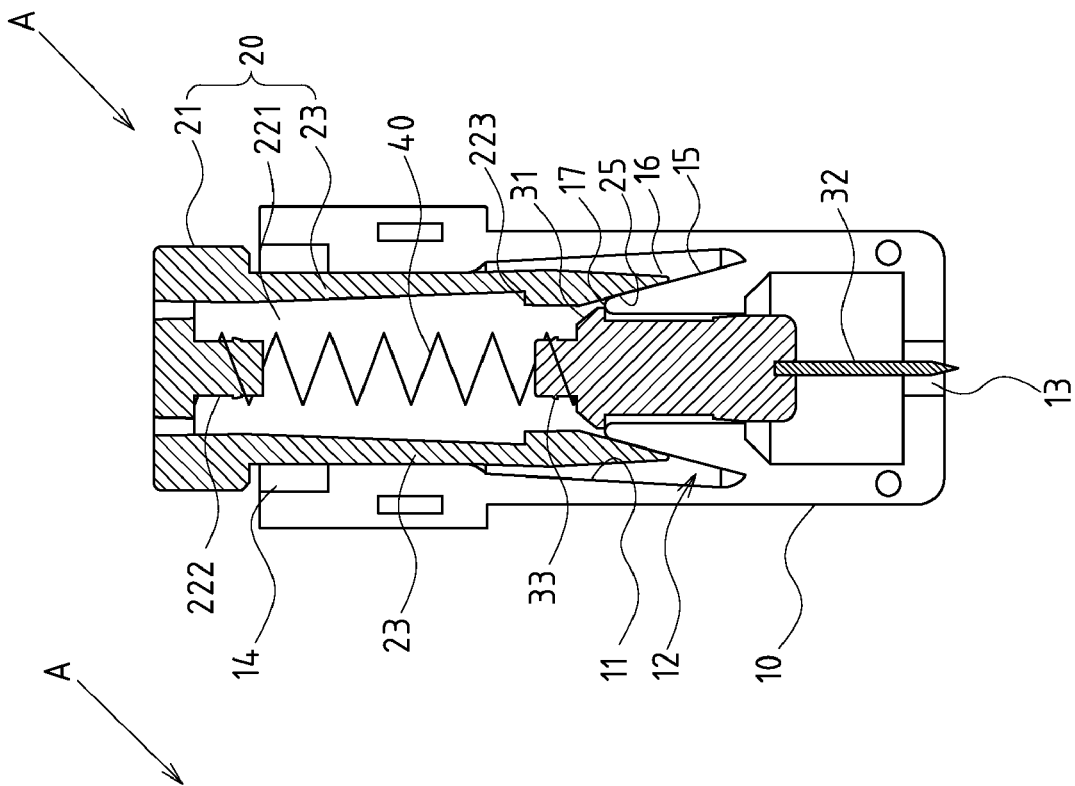
FIG. 3 shows a cross-sectional view of the assembled preferred embodiment of the present invention.
Figure 4:
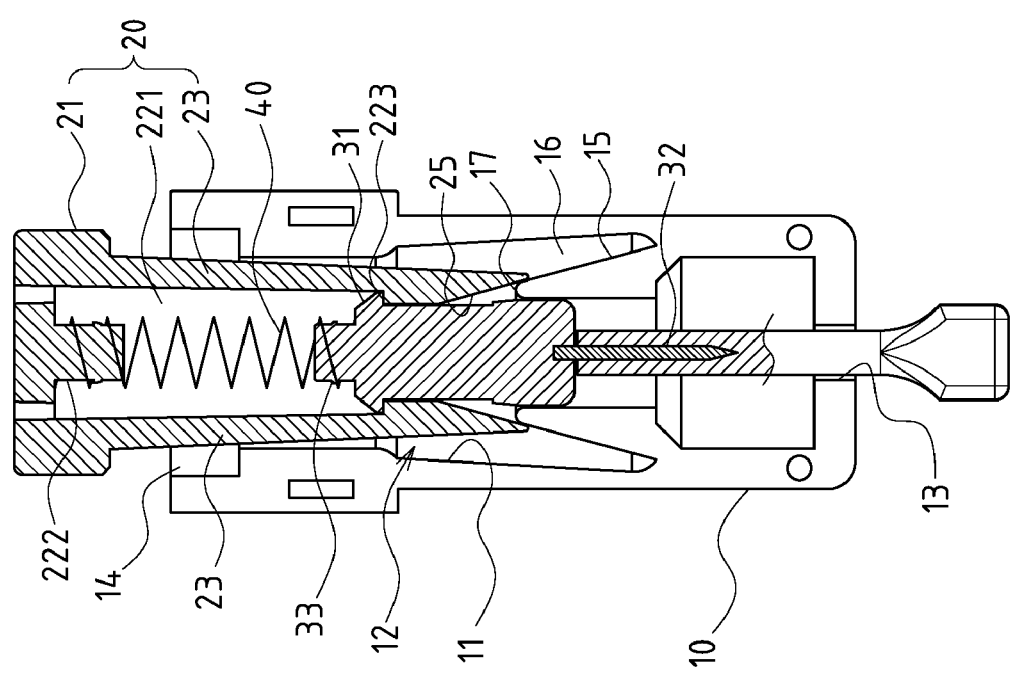
FIG. 4 shows a schematic view of the preferred embodiment of the present invention.

Based on above-specified structural configuration, the present invention is operated as follows:

Referring to FIGS. 3 and 4, the user firstly presses the control end 21 of the trigger seat 20, so that the rod 22 of the trigger seat 20 moves downwards. Meanwhile, two elastic release blades 23 are accommodated into the release groove 16, so the abutting bevel edge 25 is mated with the tapered end-face 15 of the release groove 16. With this configuration, two elastic release blades 23 are supported outwards, such that the coupling end 31 of the needle stand 30 can be disengaged from the shoulder 223 of the axial chamber 221. In such a case, the elastic resetter 40 is under an elastic release state, so the pricker 32 of the needle stand 30 is triggered downwards to protrude out of the needle outlet 13 and puncture the skin of the testee. Next, the pricker 32 of the needle stand 30 is subject to the elastic restoring force of the elastic resetter 40, so the needle stand 30 along with the pricker 32 shifts upwards, and the pricker 32 is retracted again into the retaining space 12 of the shell 10.

Figure 6:
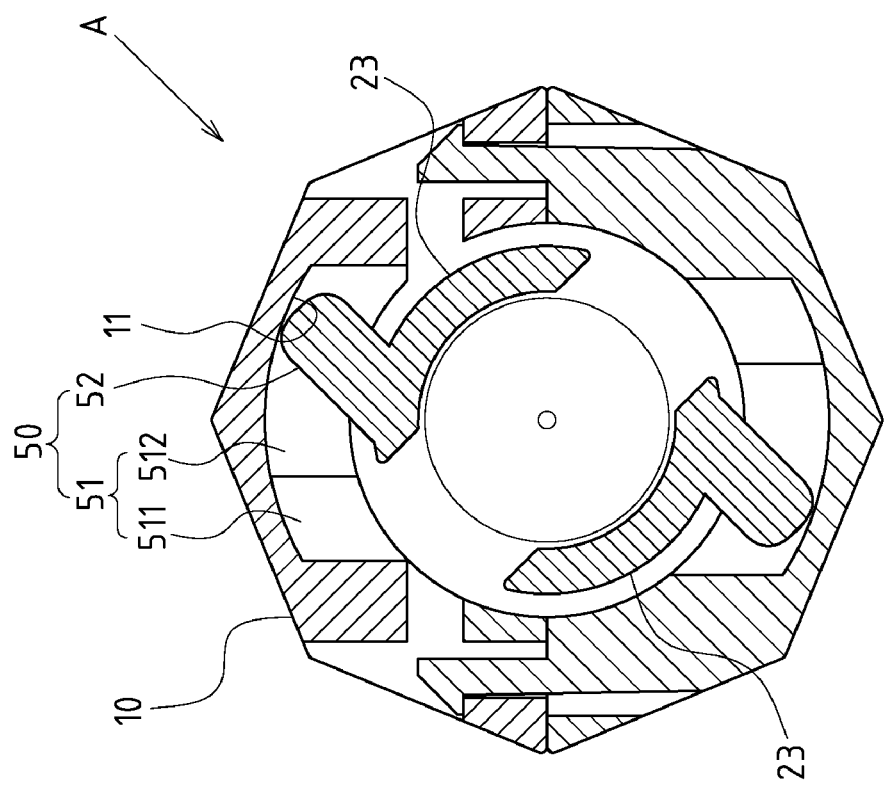
FIG. 6 shows a cross-sectional view of the present invention wherein the trigger seat is under a limiting state.

FIGS. 5 and 6 depict a schematic view of the start/stop state of the safety switching member 50. Referring to FIG. 5, when the locking bulge 52 of the safety switching member 50 is aligned with the axial dent 511 of the limiting slot 51, the trigger seat 20 is under a moveable state. Referring to FIG. 6, when the locking bulge 52 of the safety switching member 50 is aligned with the annular dent 512 of the limiting slot 51, the trigger seat 20 is under a limiting state, so the safety switching member 50 guarantees satisfactory safety functions of the blood sampling needle A since the pricker 32 cannot be triggered easily.

We claim:

1. A blood sampling apparatus comprising:
   a shell having an inner wall and a retaining space, said retaining space having a needle outlet at one end and an insertion end at an opposite end thereof;
   a through-flange protruding inwardly from said inner wall of said shell, said through-flange having a tapered end face formed thereon adjacent said inner wall of said shell, said tapered end face and said inner wall defining a release groove;
   a trigger seat movable mounted into said retaining space of said shell, said trigger seat having a control end and a rod, said rod having an axial chamber opening thereon such that a pair of elastic release blades are formed thereon, said pair of elastic release blades being respectively received into said release groove;
   an abutting bevel edge positioned at a bottom of the elastic release blade, said abutting bevel edge mated with said tapered end face;
   a needle stand having a coupling end and a pricker, said coupling end positioned in said axial chamber of said trigger seat;
   an elastic resetter assembled between said axial chamber of said trigger seat and said needle stand, said elastic resetter being in a state of accumulating elastic force such that said needle stand can be driven to reset inwardly after the elastic force is released from said state; and
   a safety switching member suitable for displacing said trigger seat and for allowing said pricker to protrude outwardly of said needle outlet of said shell, said safety switching member having a limiting slot and a pair of locking bulges, said limiting slot formed on said inner wall of said shell, said pair of locking bulges being arranged on a wall of said rod of said trigger seat corresponding to said axial chamber, said limiting slot formed an axial indent and an annular indent.

2. The blood sampling apparatus of claim 1, said annular indent of said limiting slot extending transversely.

3. The blood sampling apparatus of claim 1, said elastic resetter having a first end and a second end separately connected to one end of said needle stand and to a boss set on said axial chamber of said trigger seat.

4. The blood sampling apparatus of claim 1, said axial chamber of said trigger seat having a shoulder formed thereon, said shoulder supporting said coupling end of said needle stand.

5. The blood sampling apparatus of claim 1, wherein an exterior of said insertion end of said shell and said control end of said trigger seat being matchable together.

6. The blood sampling apparatus of claim 1, further comprising:

a pricker set sleeved externally onto said pricker of said needle stand such that said pricker set is inserted toward said retaining space of said needle outlet of said shell and producing outwardly of said needle outlet.

* * * * *